US00PP12021P2

(12) United States Plant Patent

Lim et al.

(10) Patent No.: US PP12,021 P2

(45) Date of Patent: Jul. 31, 2001

(54) PEACH TREE 'SPRINTER'

(76) Inventors: Jung-Kyoung Lim; Soon-Ja Im You, both of 637-1 Woulhari, Seomyun, Yunkikun, Chungnam (KR)

( * ) Notice: Subject to any disclaimer, the term of this patent is extended or adjusted under 35 U.S.C. 154(b) by 0 days.

(21) Appl. No.: 09/217,599

(22) Filed: Dec. 21, 1998

(51) Int. Cl.[7] ..... A01H 5/00

(52) U.S. Cl. ..... Plt./195

(58) Field of Search ..... Plt./195

(56) References Cited

PUBLICATIONS

Kim, Cho, Lee, & Yu, Report on the Peach Tree "Yumyeong" by in the Horticultural Experiment Station, Suwon, Korea.

Jung–Kyoung Lim, Plant Belonging To New Variety Of Peach Tree, Aug. 1, 1989, Korean Industrial Property Office.

*Primary Examiner*—Bruce R. Campell

*Assistant Examiner*—Melissa L. Kimball

(74) *Attorney, Agent, or Firm*—Gilberto M. Villacorta; Pepper Hamilton LLP; Paul D. Roath

(57) ABSTRACT

A new and distinct variety of peach *Prunus persica* tree with the following combination of unique features that are desirable in a new variety.

1. Heavy and regular production of fruit.
2. Production of very firm, white flesh fruit with good handling and shipping quality.
3. Fruit that will stay firm on the tree 10 to 17 days after maturity (shipping ripe).
4. Fruit with excellent flavor and eating quality.
5. Middle season maturity of white flesh fruit.
6. Fruit having a skin with pink overspread with light yellow.
7. Vigorous half-open growth.

2 Drawing Sheets

BACKGROUND OF VARIETY

In the country of origin, Republic of Korea, the tree of this disclosure is believed to have been derived from the Korean commercial variety 'Weolme', which has been patented in Korea (Patent No. 52872) and within the subspecies 'dianthiflora' (Dipp.); and originated in Seomyun, Yunkikun, Chungnam, Republic of Korea. The appropriate botanical classification for this tree is believed to be *Prunus persica* . This subject tree is believed to be exceptional in a number of characteristics and will offer a further option to commercial growers of stone fruits in terms of fruit having large to very large size, firm flesh, clingstone, sweeter than the fruit of the parent tree, 'Weolme', attractively colored fruit which has a comparatively high capacity to withstand handling, shipping and storage. Having the additional desirable fruit characteristics of heavy production of fruit with an attractive round shape and pleasant, sweet taste, and which is harvested earlier than normal harvest for fruit of extra large size, this tree promises to be a valuable new variety to industry and commerce which has value as a dessert variety but which may also be used as a canner. This tree further has the advantage of being mid to late-season in blooming so that it is less susceptible to late frosts than other locally adapted tree varieties. We are not aware of varieties which offer a similar or comparable combination of characteristics.

ORIGIN OF THE VARIETY

The new tree was selected from among several thousand seedlings from 'Weolme' variety, which had been planted on our farm in Seomyun, Yunkikun, Chungnam, Korea. The seedling was discovered near a specimen of the noted apparent seed parent, which is an early season variety and which normally ripens between July 20 to August 5, which is 5 days earlier than 'Weolme'. Our attention was drawn to this tree when we noticed that the skin of the fruit was very smooth; producing regular form and sweeter by about 0.5 to 1°(Bx) than the parent 'Weolme' variety on the wood. 'Weolme' is influenced by temperature and rain at the time of pollination, thereby resulting in production of irregular form of the fruit, whereas the present 'Sprinter' is not affected by weather conditions such as temperature, rain etc. Based on these observations, we selected the variety for asexual reproduction and commercialization.

ASEXUAL REPRODUCTION OF THE VARIETY

Asexual reproduction of the new and distinct variety was performed by budding or grafting in our orchard located in Seomyun, Yunkikun, Chungnam, Korea and shows that all characteristics run true to the original tree and are established and transmitted through succeeding propagation.

SUMMARY OF THE VARIETY

The present new and distinct variety of peach tree has been denominated 'Sprinter', and the height of the fully grown tree about 3 to 3.5 meters, which is almost same with that of the tree, 'Yumyeong'. The diameter of the new tree is about 6 to 7 meters. This tree grows vigorously on standard peach rootstock, with a half open shape and is a regular and productive bearer of extra large, skin with pink overspread with light yellow, white flesh, clingstone fruit with a mild, sweet subacidic flavor with excellent eating and stock quality. The fruit is further characterized by having very firm flesh, the ability to hang on the tree 10 to 17 days after maturity (shipping ripe), having good handling and shipping quality, approximately 5 days after 'Weolme', and 30 days before 'Yumyeong', which are established commercial varieties in Korea.

DESCRIPTION OF THE PHOTOGRAPHS

FIG. 1 shows typical specimens of the fruit of the new and distinct peach variety; and typical leaf from the tree, 'Sprinter'. The illustrations show an exterior of the fruit and a fruit divided in its suture plane to reveal flesh coloration, pit cavity, and a stone remaining in place. The photographic illustration was taken shortly after being picked (firm ripe);

Figure 1:
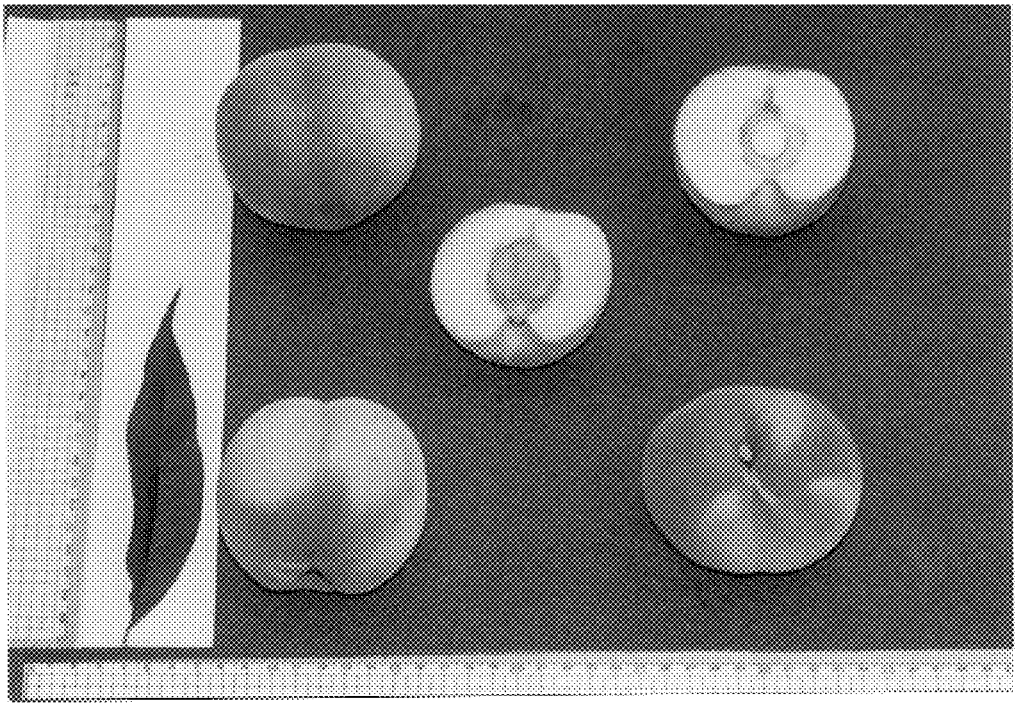
Figure 2:
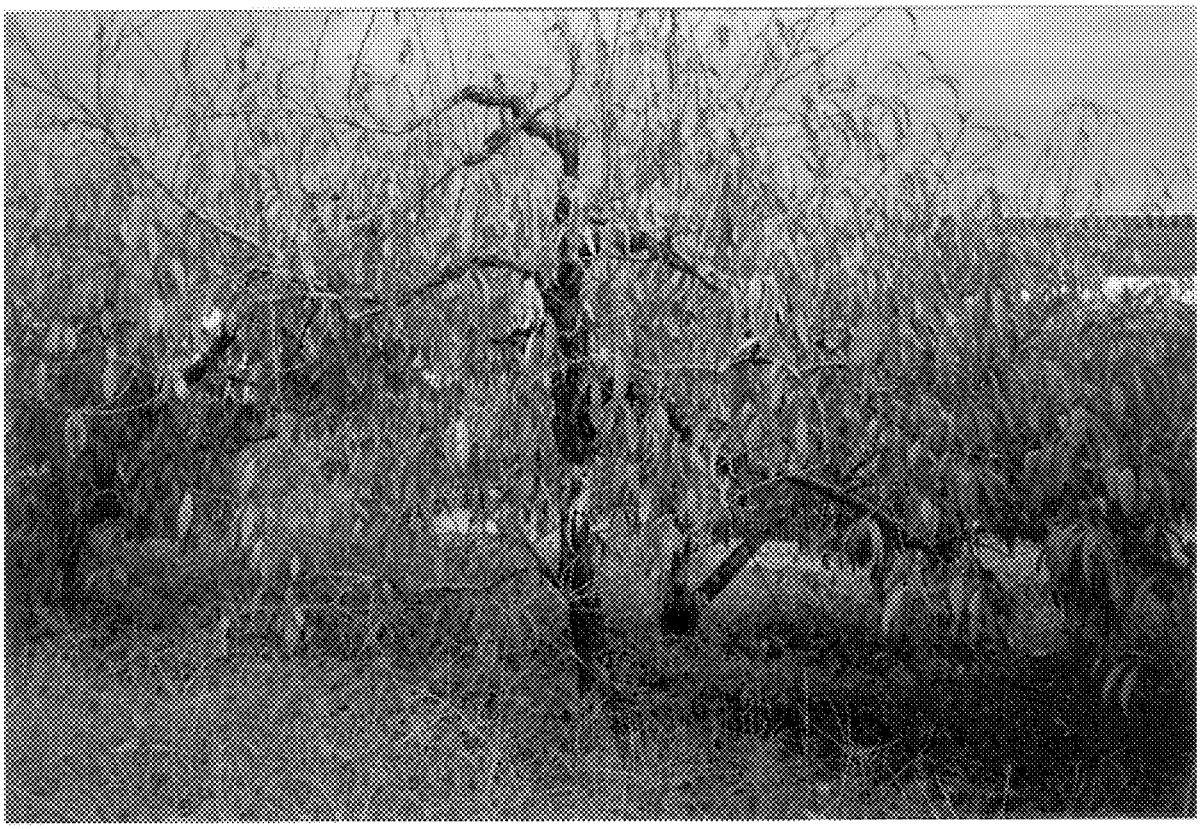
FIG. 2 shows a peach tree 'Sprinter'. The photographic illustration was taken after almost all the leaves had fallen.
Figure 3:
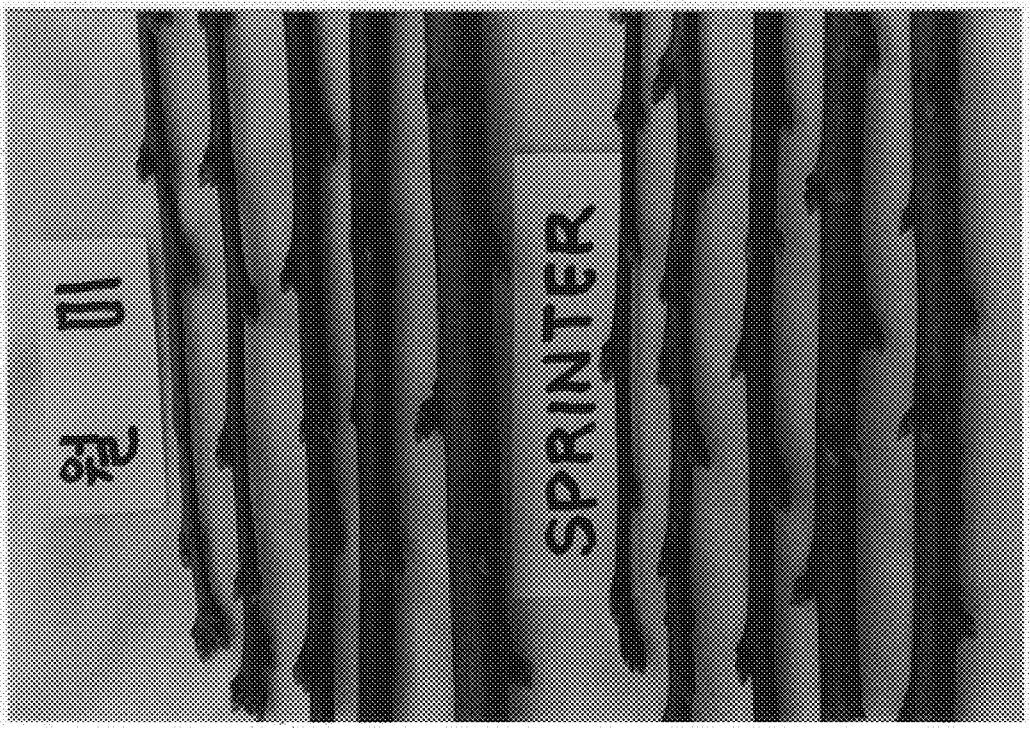
FIG. 3 depicts the comparative picture of sprouts between the parent tree 'Weolme'and the present tree 'Sprinter'.

The color in the photographs are as nearly true as is reasonably possible in a color representation of this type.

DESCRIPTION OF THE VARIETY

The following is a detailed botanical description of the new and distinct variety of peach tree, its flowers, fruit and foliage as based on observations of the specimen grown in our orchard located Seomyun, Yunkikun, Chungnam, Korea, with color terminology (except those in common terms) in accordance with Panton® Professional Color System Selector (Pantone, Inc., 1984, 1990).

Tree:
- *Size.*—Large.
- *Vigor.*—Vigorous. Having terminal growth of 1.5 to 2 meters per year, with the growth of the trunk terminating at the height of 3 to 3.5 meters in 3 or 4 years, in Chungnam, Korea.
- *Form.*—Usually pruned to half open shape. The new peach tree grows 1.5 to 2 meters every year from the first to the third year, with the trunk terminating at about 3 meters height and then the trunk thickening every year, and the branches extending upwardly at an angle of 40 to 55°, growing 1.5 meters to 2 meters a year to a maximum extent of 6 to 7 meters. Almost the same branching as with the parent tree 'Weolme'. To obtain large fruit, about 80% pruning of the flowers is necessary.
- *Production.*—Productive (about 3000 kg/10a).
- *Bearing.*—Regular.
- *Density.*—Medium dense.

Trunk:
- *Size.*—Medium to stocky.
- *Texture.*—Smooth.
- *Color.*—Brown (18-1124) to (18-1222).

Branches:
- *Size.*—Medium.
- *Texture.*—Varies from smooth to medium rough with maturity.
- *Lenticles.*—Medium size. Medium number.
- *Color.*—Brown (18-1031) to (18-1130) having small parts with light green (16-6329) to (16-6339).

Leaves:
- *Size.*—Medium to large. The shape and size are almost the same as those of the 'Weolme' variety.
- *Average length.*—14 to 16.5 cm.
- *Average width.*—2.5 to 2.7 cm.
- *Form.*—Lanceolate-pointed.
- *Texture.*—Smooth.
- *Thickness.*—Medium.
- *Margin.*—Crenate.
- *Petiole.*—Medium length. Medium thickness.
- *Glands.*—Reniform. Number varies from 0 to 5. Average number 2. Located on base of leaf blade and upper portion of petiole.
- *Color.*—Upper surface green to dark green (18-01117) to (18-0322). Lower surface dull green to grayish green (17-6319) to (17-0119).

Flower buds:
- *Size.*—Medium.
- *Form.*—Plump.
- *Length.*—Medium.
- *Pubescence.*—Pubescent.

Flowers:
- *Size.*—Medium non-showy.
- *Blooming period.*—This variety has the same flowering as the 'Weolme' peach tree. The tree is self-fertile so it does not require artificial pollination.
- *Color.*—Pale Pink.
- *Pollen.*—Abundant.
- *Number of Pedals.*—5.

Fruit:
- *Maturity when described.*—Firm ripe.
- *Date of first picking.*—Jul. 20, 1998.
- *Date of last picking.*—Aug. 5, 1998.
- *Size.*—Extra large. Average diameter axially 8.5 to 12.5 cm. Average transversely in suture plane 8.0 to 12.0 cm.
- *Form.*—Globose — slightly tip at apex and slightly flattened the stem end. The fruit is exceptionally symmetrical.
- *Suture.*—Shallow but pronounced, extends from base to apex.
- *Ventral surface.*—Nearly rounded, very slightly lipped.
- *Apex.*—Varies from rounded to slight pistil point.
- *Base.*—Retuse.
- *Cavity.*—Rounded to slightly elongated in suture plane. Average depth—1.5 cm. Average breadth 2.0 cm.

Skin:
- *Thickness.*—Medium.
- *Texture.*—Tenacious to flesh.
- *Tendency to crack.*—None.
- *Down.*—Moderate amount, short to very short in length.
- *Color.*—Pink (17-1654) to (17-1562). Overspread with light yellow.

Flesh:
- *Texture.*—Very firm.
- *Ripens.*—Evenly.
- *Fibers.*—Small, tender.
- *Juice.*—Moderate.
- *Flavor.*—Excellent, mild, very sweet.
- *Aroma.*—Moderate.
- *Eating quality.*—Excellent.
- *Amygdalin.*—*Undetected.*
- *Color.*—White to milky white (no Pantone number) to (11-0507).

Stone:
- *Type.*—Cling stone.
- *Size.*—Large. Average length 2.7 cm. Average width 2.6 cm. Average thickness 1.7 cm.
- *Form.*—Ovoid.
- *Base.*—Mostly straight — some rounded.
- *Apex.*—Acuminate.
- *Sides.*—Equal.
- *Surface.*—Irregularly furrowed toward apex, ridges usually rounded, pitted toward base.
- *Tendency to split.*—None.
- *Color.*—Brown to reddish brown (18-1540) to (19-1540).

Use: The fruit of the present new variety is well suited for novelty, processing and canning, as well as for use as a dessert peach. Market — Local and long distance.
Keeping quality: Very good.
Shipping quality: Very good.

The new and distinct variety of peach tree, its foliage and fruit described above may vary in slight detail due to variations in climate, soil conditions and cultural practices under which the variety may be grown. The botanical description above is that of the variety grown under the ecological conditions prevailing near Seomyun, Yunkikun, Chungnam, Korea.

We claim:

1. A new and distinct variety of peach tree, substantially as illustrated and described, characterized in that the tree is large, grows vigorously with a half open shape and is a regular and productive bearer of large, middle season maturing, white flesh, clingstone fruit with excellent flavor and eating quality; the fruit is further characterized in that it has very firm flesh, good handling and shipping quality and it has a skin with pink overspread with light yellow.

* * * * *